****

US011120892B2

(12) United States Patent
Polesskiy et al.

(10) Patent No.: US 11,120,892 B2
(45) Date of Patent: Sep. 14, 2021

(54) CONTENT TESTING DURING IMAGE PRODUCTION

(71) Applicant: Amazon Technologies, Inc., Seattle, WA (US)

(72) Inventors: Aleksey A. Polesskiy, Seattle, WA (US); Christopher David Byskal, Issaquah, WA (US)

(73) Assignee: Amazon Technologies, Inc., Seattle, WA (US)

( * ) Notice: Subject to any disclaimer, the term of this patent is extended or adjusted under 35 U.S.C. 154(b) by 163 days.

(21) Appl. No.: 14/743,648

(22) Filed: Jun. 18, 2015

(65) Prior Publication Data

US 2016/0371433 A1 Dec. 22, 2016

(51) Int. Cl.
*G16B 45/00* (2019.01)
*G06F 9/455* (2018.01)
(Continued)

(52) U.S. Cl.
CPC ............ *G16B 45/00* (2019.02); *A63F 13/212* (2014.09); *A63F 13/23* (2014.09); *A63F 13/79* (2014.09);
(Continued)

(58) Field of Classification Search
CPC . G16B 45/00; G06F 9/45558; G06F 9/45533; G06F 3/048; G06F 2009/45562;
(Continued)

(56) References Cited

U.S. PATENT DOCUMENTS 7,856,440 B2 * 12/2010 Alpern ................... G06F 16/00
707/756
8,620,870 B2 12/2013 Dwarampudi et al.
(Continued)

FOREIGN PATENT DOCUMENTS

CN 103853595 A 6/2014
JP 2009-075877 A 4/2009
(Continued)

OTHER PUBLICATIONS

Singapore Patent Application No. 11201710207V; Written Opinion and Search Report; dated Apr. 25, 2018; 7 pages.
(Continued)

*Primary Examiner* — Theodore C Parsons
*Assistant Examiner* — Bruce S Ashley
(74) *Attorney, Agent, or Firm* — BakerHostetler

(57) ABSTRACT

Techniques for content testing during image production are described herein. Information associated with a content item may be loaded onto a first virtual machine instance and a second virtual machine instance. On the second virtual machine instance, production of a virtual machine image including the information associated with the content item may be initiated. On the first virtual machine instance, a first instance of the content item may be executed. At least part of a time during which the first instance of the content item is executed may occur during the production of the virtual machine image. Upon completion of production of the virtual machine image and approval of its use, the virtual machine image may be replicated onto other content item instances, and the first virtual machine instance may be terminated or repurposed.

14 Claims, 7 Drawing Sheets

(51) Int. Cl.
*A63F 13/212* (2014.01)
*A63F 13/23* (2014.01)
*A63F 13/79* (2014.01)
*A63F 13/825* (2014.01)
*G06F 3/048* (2013.01)

(52) U.S. Cl.
CPC ............ *A63F 13/825* (2014.09); *G06F 3/048* (2013.01); *G06F 9/45533* (2013.01); *G06F 9/45558* (2013.01); *G06F 2009/45562* (2013.01)

(58) Field of Classification Search
CPC ........ A63F 13/212; A63F 13/23; A63F 13/79; A63F 13/825
See application file for complete search history.

(56) References Cited

U.S. PATENT DOCUMENTS

| | | | |
|---|---|---|---|
| 2009/0259855 A1* | 10/2009 | de Cesare | G06F 21/51 713/189 |
| 2010/0100881 A1* | 4/2010 | Shigeta | G06F 11/2247 718/1 |
| 2011/0004676 A1 | 1/2011 | Kawato | |
| 2012/0072780 A1 | 3/2012 | Kini et al. | |
| 2012/0084414 A1 | 4/2012 | Brock et al. | |
| 2012/0096104 A1* | 4/2012 | Hironaka | H04N 21/4424 709/212 |
| 2012/0110574 A1 | 5/2012 | Kumar | |
| 2012/0159423 A1* | 6/2012 | Becker | G06F 9/44526 717/102 |
| 2012/0246640 A1 | 9/2012 | Marshall et al. | |
| 2013/0007731 A1 | 1/2013 | Fries | |
| 2013/0086578 A1* | 4/2013 | Eilam | G06F 9/45558 718/1 |
| 2013/0297922 A1* | 11/2013 | Friedman | G06F 8/63 713/2 |
| 2014/0040887 A1* | 2/2014 | Morariu | G06F 9/44505 718/1 |
| 2014/0101754 A1 | 4/2014 | McKenzie et al. | |
| 2014/0189641 A1 | 7/2014 | Anderson et al. | |
| 2014/0342819 A1 | 11/2014 | Bruno, Jr. et al. | |
| 2015/0163270 A1* | 6/2015 | Lyons | H04L 65/60 463/42 |
| 2016/0094720 A1 | 3/2016 | Girard et al. | |
| 2016/0364554 A1* | 12/2016 | Lincoln | G06F 21/121 |

FOREIGN PATENT DOCUMENTS

| | | |
|---|---|---|
| JP | 2011-123891 A | 6/2011 |
| JP | 2011-210032 A | 10/2011 |
| WO | WO 2009/098909 A1 | 8/2009 |

OTHER PUBLICATIONS

Hansen et al.; "The Laundromat Model for Automatic Cluster Computing"; IEEE Int'l Conf. on Automatic Computing; 2006; 10 pages.

International Patent Application No. PCT/US2016/037419; Int'l Preliminary Report on Patentability; dated Dec. 28, 2017; 8 pages.

* cited by examiner

CONTENT TESTING DURING IMAGE PRODUCTION

BACKGROUND

In recent years, the use of electronically presented content, such as video games, has become increasingly popular and widespread. In some examples, it may be desirable to have several instances of a content item executing simultaneously. This may occur, for example, when large numbers of users want to interact with the content item. For example, in some cases, one or more players may compete in a first instance of a video game, while one or more other players may compete in a second instance of the same video game. Although the underlying code used to execute each instance of the video game may be identical, the players within the different instances may be provided with separate and independent experiences. For example, at any given time, players in the first and second instances of the video game may be competing in different virtual locations, against different characters, at different levels of progress, and under various other different conditions.

One potential technique for generating a fleet of multiple instances of a content item involves the creation of a virtual machine image that includes the underlying binaries or other code associated with the content item. The virtual machine image may be advantageous because, for example, it may allow the content item to be easily and efficiently replicated onto large numbers of other virtual machines, thereby allowing large numbers of content item instances to scale up quickly in response to user demand. However, one drawback of a virtual machine image is that, depending upon the size of the content item code being included in the image, a substantial delay time may sometimes be required in order to produce the virtual machine image before it can be activated and replicated for execution.

BRIEF DESCRIPTION OF DRAWINGS

The following detailed description may be better understood when read in conjunction with the appended drawings. For the purposes of illustration, there are shown in the drawings example embodiments of various aspects of the disclosure; however, the invention is not limited to the specific methods and instrumentalities disclosed.

DETAILED DESCRIPTION

Figure 1:
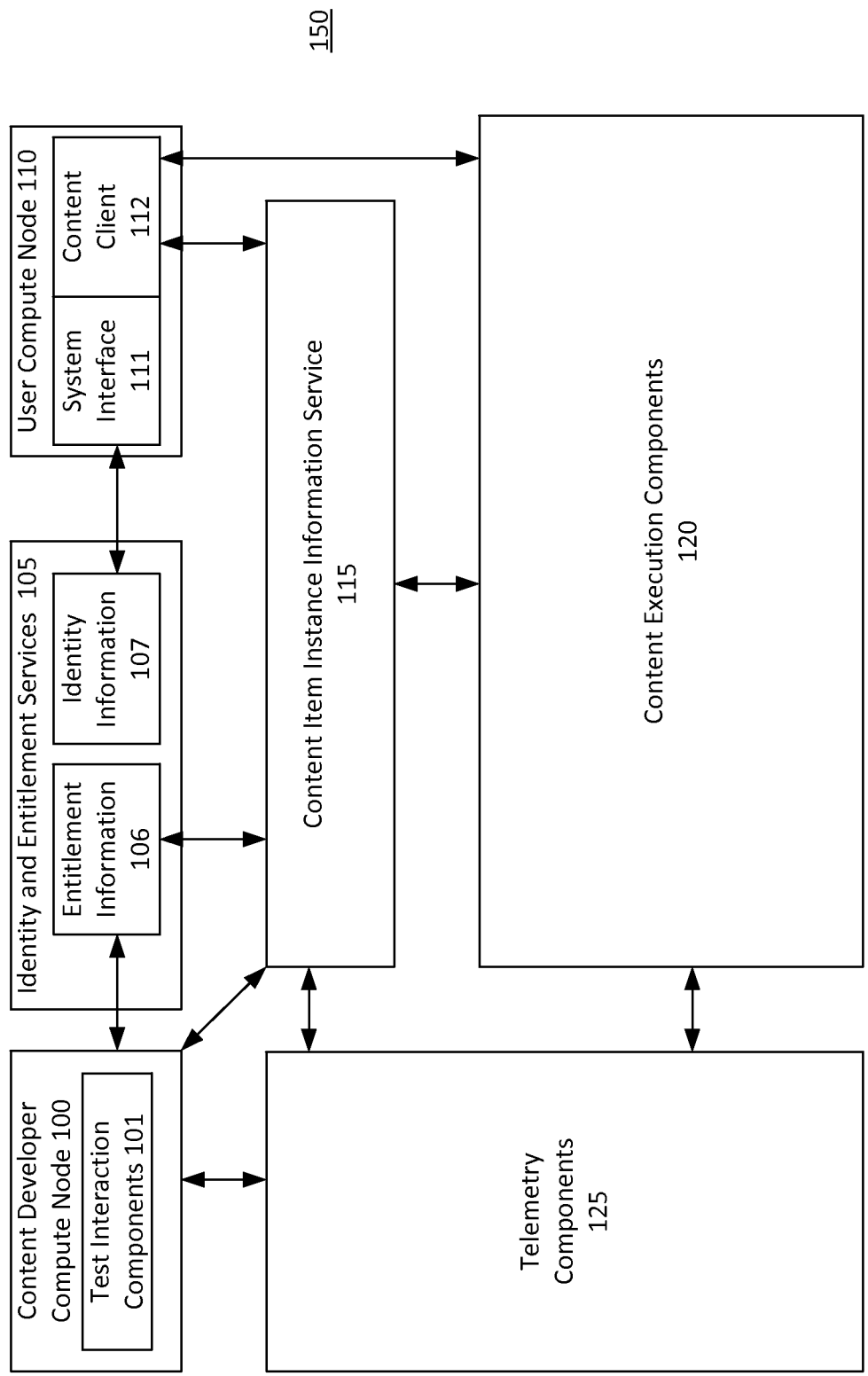
FIG. 1 is a diagram illustrating an example content deployment, scaling and telemetry system that may be used in accordance with the present disclosure.

Techniques for content testing during image production are described herein. In some examples, an indication may be received from a developer that a content item, such as a video game, is ready for deployment to users by a backend service. In response to this indication, the service may load code, binary files, and/or other content item information to a first virtual machine instance. A snapshot of the content item information may then be taken and copied to a second virtual machine instance, which may then be used to produce a virtual machine image associated with the content item. The virtual machine image may, for example, allow the content item to be easily and efficiently replicated onto large numbers of other virtual machine instances, thereby allowing large numbers of content item instances to scale up quickly in response to user demand. However, as set forth above, a substantial time may, in some cases, be required to produce the virtual machine image.

According the described techniques, during at least part of the time in which the virtual machine image is being produced, the first virtual machine instance may be used to execute a content item instance, referred to herein as a test content item instance. The test content item instance may be made available to developers and may, for example, allow developers to experience the benefits of the virtual machine image without having to wait until the image is fully produced in order to test or otherwise interact with the content item. Additionally, the test content item instance may, in some cases, allow developers to test and interact with a content item instance that is executed by the same backend service that will potentially host the activated content item fleet, thereby allowing developers to test and interact with the content item in the same environment in which it may be provided to other users.

In some examples, prior to execution of the test content item instance, the content item information on the first virtual machine instance may be examined to confirm that the content item has been created using an approved software development kit (SDK) and to detect a particular version of the SDK. As will be described in greater detail below, an approved SDK in this context may be an SDK that is integrated with a backend service that will potentially host the activated content item fleet. An approved SDK may provide functionality built-in to the content item that may, for example, allow ingestion, configuration, provisioning and deployment of the content to be more easily and rapidly accomplished, such as by allowing the content to interact more efficiently with a multi-player video gaming or other multi-user environment. For example, an approved SDK may assist in reporting of information associated with executing instances of the content item. In addition to detection and approval of an SDK, one or more proxy components may be installed on the first virtual machine instance prior to execution of the test content item instance. The installed proxy components may further assist with efficient hosting of the content item by the backend service.

In some cases, the test content item instance may allow testing of the content item such that one or more flaws or other problems may be quickly identified and efficiently corrected. Also, in some cases, the test content item instance may provide the developer with additional opportunities to interact with the content item and to confirm whether or not the developer wishes to approve the virtual machine image for use. When a developer approves the virtual machine image for use, the test virtual machine instance may be terminated and/or repurposed, and the virtual machine image may be replicated as desired for generation of the content item instance fleet. By contrast, in some cases, a developer may experience a change of heart and decide not approve the use of the virtual machine image, thereby saving potential unnecessary costs.

A diagram of an example content deployment, scaling and telemetry system 150 that may be used in accordance with the present disclosure is shown in FIG. 1. As shown, content developer compute node 100 may include, for example, various interfaces, consoles, and/or dashboards operated by content developers or other parties. User compute node 110 may communicate with identity and entitlement services 105, content item instance information service 115, and/or telemetry components 125 using, for example, one or more networks, including one or more wide area networks (WANs) such as the Internet and/or one or more local area networks (LANs). As should be appreciated, although only a single developer compute node 100 is shown in FIG. 1, system 150 may include any number of different developers and other parties deploying any number of different content items. In some cases, content developer compute nodes 100 may execute one or more integrated development environment (IDE) applications, or portions thereof, to assist in development of content. Generally, as will be described in greater detail below, content developer compute node 100 may allow, for example, developers to design and develop content items, to provide access to content items for deployment, to provide user identity and/or entitlement information, to monitor and obtain feedback and metrics associated with content item instances, content item fleets, and historical information, and other operations. As will also be described in greater detail below, when a developer is ready to deploy a certain content item, information for accessing the content may, for example, be provided to content execution components 120, which may perform various operations for executing instances of the content item, which are made accessible to various users. As set forth above, in some examples, during at least part of the time that a virtual machine image associated with the content item is being produced, a test content item instance may be executed that may, for example, allow a developer to conduct additional testing on the content item. Test interaction components 101 may, in some examples, allow the developer to interact with the test content item instance, to indicate approval or disapproval of use of the virtual machine image, and to perform other developer operations set forth herein in association with the test content item instance.

In some examples, in addition to developing and providing of content, developers and other parties may also provide identity and/or entitlement information for various users to access the provided content. In particular, developer compute node 100 may sometimes interact with identity and entitlement services 105 to provide this identity and/or entitlement information. In other examples, information may be provided to identity and entitlement services 105 by other parties. In some cases, developers or other parties may configure an identity pool by providing indications of authorized users that may access one or more content items. In some examples, identity and entitlement services 105 may generate or receive identity authentication information, such as user names, passwords, and the like, for authenticating the identities of various users. User identities and their associated authentication information may be stored, for example, in identity information 107. Also, in some examples, developers or other parties may provide entitlement information 106, which may indicate the content items with which each authorized user is entitled to interact. In some examples, certain users may only be permitted to access test versions, or fully developed versions, certain versions for which the user has paid or subscribed, or any other types of content.

User compute node 110 may be employed by a user to request access to content, such as a user session for interaction with a particular content item instance. User compute node 110 may communicate with identity and entitlement services 105, content item instance information service 115, and/or content execution components 120 using, for example, one or more networks, including one or more wide area networks (WANs) such as the Internet and/or one or more local area networks (LANs). As should be appreciated, although only a single user compute node 110 is shown in FIG. 1, system 150 may include any number of different users accessing the same or different content. In some cases, in order for a user to requests access to content, a determination may be made of whether the user is authorized to access content that is deployed by system 150. In some examples, system interface 111 may provide identity authentication information for the user to identity and entitlement services 105, which may attempt to match the provided user identity authentication information to identity authentication information for the user that is stored in identity information 107. If no match is determined, then the user may, for example, be denied access to any content and/or may be prompted to register, pay, and/or subscribe for access to content and/or may be redirected to various services for performing those operations. If, on the other hand, the user's provided identity authentication is matched to stored identity authentication information, then the user's identity may be authenticated and the user may be permitted to further interact with system 150 and request access to content.

Content client 112 of user compute node 110 may then communicate with content item instance information service 115 to provide information about the user to content item instance information service 115. In turn, content item instance information service 115 may communicate with identity and entitlement services 105 to determine, based at least in part on entitlement information 106, content that the user is authorized for and entitled to access. As will be described in greater detail below, the user may then request access to a selected content item that the user is entitled access, and content item instance information service 115 may match and assign a user session for the user to a particular instance of the selected content item that executes within content execution components 120. This assignment information may be forwarded to content execution components 120, which may establish communications between content client 112 and its assigned matched content item instance.

In addition to scaling and executing of content, content execution components 120 may also collect various telemetry information about executing content item instances, such as a number of occupied user sessions, a number of unoccupied user sessions, content item instance duration, memory usage, and the like. Content execution components 120 may provide this collected telemetry information to telemetry components 125, which, as will be described in greater detail below, may route and process the telemetry data. For example, telemetry components may provide content item instance information to content item instance information service 115. This content item instance information may, for example, enable matching and assignment of user sessions to content item instances, launching of new content item instances, and content item instance-level feedback and metrics to content developers and other parties. In addition to content item instance information service 115, telemetry information may also be provided to other services, such a content item fleet information service and a historical information service. These and other telemetry data services are described in greater detail below with reference to FIG. 3.

Figure 2:
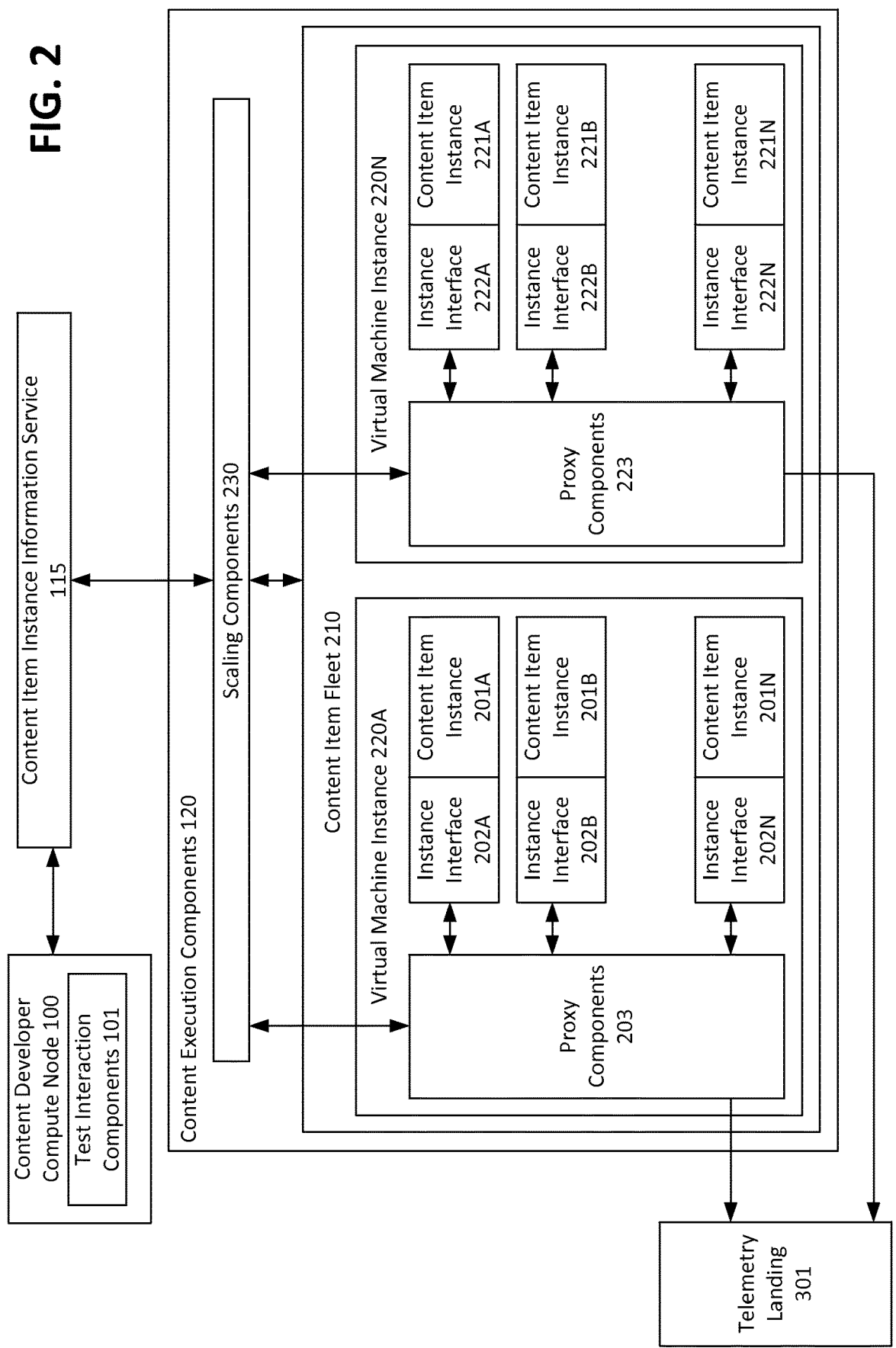
FIG. 2 is a diagram showing an example content scaling and execution system that may be used in accordance with the present disclosure.

FIG. 2 is a diagram showing an example content scaling and execution system that may be used in accordance with the present disclosure. As shown in FIG. 2, content execution components 120 (also shown in FIG. 1) include scaling components 230, which may perform various operations for scaling deployed content. In particular, when a content item is ready for deployment using system 150, a message may be sent via developer compute node 100 indicating that the content item is ready for deployment and providing information for accessing the content, such as location and/or address information. In some examples, the developer may also provide additional information such as a name for the content item fleet, a development stage, and a description of the content item. The access information and, in some cases, additional information may be provided to content scaling component 230, which may issue instructions to install one or more instances of the content item as an image on a virtual machine instance. As will be described in greater detail below, additional instances of the content item may then be launched on the same virtual machine instance and/or by copying the image onto any number of additional virtual machines instances.

A grouping of content item instances for the deployed content item is referred to as the content item fleet. In FIG. 2, content execution components 120 execute an example content item fleet 210. As should be appreciated, although only a single content item fleet 210 is shown in FIG. 2, content execution components 120 may execute any number of different content item fleets at the same or different times. In the particular example of FIG. 2, content item fleet 210 includes two virtual machine instances 220A and 220N, each executing three content item instances. In particular, virtual machine instance 220A executes content item instances 201A-N, while virtual machine instance 220N executes content item instances 221A-N. It is noted, however, that a content item fleet in accordance with the disclosed techniques may include any number of virtual machine instances each executing any number of different content item instances. In some examples, one or more of content item instances 201A-N and 221A-N, and in some cases all of content item instances 201A-N and 221A-N, may be configurable to execute with multiple simultaneously assigned users sessions. This may, for example, allow multiple users to play with or against one another, or to otherwise collaborate within a single content item instance, such as may occur in a multiplayer video game or other multi-user applications.

In some examples, each content item instance 201A-N and 221A-N may receive input, such as control input (e.g., character movement, weapons firing, menu selections, etc.), from its assigned user sessions. Also, in some examples, each content item instance 201A-N and 221A-N may then transmit content information, such as state data updates, event data updates and other information to user compute nodes for the assigned user sessions. The user compute nodes may use this data to render and present content at their respective content compute nodes. In some examples, each user node may include one or more graphics processing units (GPUs) for rendering of graphics data associated with the content item.

In some other examples, content may be rendered by content execution components 120 based on content information that is generated and/or maintained by the content item instances 201A-N and 221A-N. In these examples, content item instances 201A-N and 221A-N may, in some cases, each have access to one or more GPUs. The rendered content may then be transmitted by the content item instances 201A-N and 221A-N to user compute nodes for the assigned user sessions.

As shown in FIG. 2, each content item instance 201A-N and 221A-N includes a respective instance interface 202A-N and 222A-N. In some examples, each instance interface 202A-N and 222A-N may be associated with and/or implemented using a software development kit (SDK) and may assist in enabling configuration of a content item instance, initiation of user sessions in the content item instance, and collection of information from the content item instance, such as telemetry information. For example, in some cases, various instructions associated with instance interfaces 202A-N and 222A-N, such as one or more SDKs, may be exposed and/or provided to developers. These instructions may assist in enabling the content item instances 201A-N and 221A-N to perform the tasks described above and possibly other tasks. The developers may, in turn, include, embed or otherwise associate these instructions with the content item that is made accessible for deployment. Telemetry information provided by instance interfaces 202A-N and 222A-N may include, for example, information about executing content item instances, such as a number of occupied user sessions, a number of unoccupied user sessions, content item instance duration, memory usage, and the like.

As also shown in FIG. 2, instance interfaces 202A-N may communicate with proxy component 203 for virtual machine instance 220A, while instance interfaces 222A-N may communicate with a proxy component 223 for virtual machine instance 220N. Proxy components 203 and 223 may generally allow exchange of information and commands between content item instances 201A-N and 221A-N and components external to virtual machine instances 220A-N, such as scaling components 230 and telemetry landing 301. In particular, in some examples, proxy components 203 and 223 may receive commands from scaling components 230, such as commands to launch content item instances and commands to add a user sessions to a particular content item instance. In some examples, proxy components 203 and 223 may also provide information to scaling components 230 and/or telemetry landing 301 about executing content item instances. The information provided by proxy components 203 and 223 may include, for example, any of the information collected by instance interfaces 202A-N and 222A-N, such as any of the telemetry information described above or other relevant information. Proxy components 203 and 223 may provide content item instance information at any desired interval, such as at regular repeating intervals (e.g., every minute or every five minutes), in response to particular events or conditions, in continuous or intermittent streams, or using any combination of these or other techniques.

In some examples, scaling components 230 may monitor content item fleet 210 based on, for example, information provided by proxy components 203 and 223 such as described above. In some cases, scaling components 230 may use this information to automatically scale content item fleet 210 by allocating additional virtual machine instances and/or content item instances to the content item fleet 210 and/or by de-allocating existing virtual machine instances and/or content item instances from the content item fleet 210. In some examples, certain configurable conditions may cause scaling components 230 to allocate additional virtual machine instances and/or content item instances to a content item fleet. These conditions may include for example, determining that the total and/or average number of unoccupied user sessions for all content item instances in the fleet have met or dropped below a particular quantity, determining that the total number of unoccupied user sessions for one or more individual content item instances in the fleet have met or dropped below a particular quantity, and/or other conditions. Also, in some examples, scaling components 230 may allocate additional virtual machine instances and/or content item instances to a content item fleet based on a determination that a particular sub-set of a content item fleet, such as a sub-set of content item instances having particular content attributes (e.g., modes, virtual locations, characters, weapons, plot lines, story arcs, etc.) meets any of the example allocation conditions described above or other conditions.

Also, in some examples, certain configurable conditions may cause scaling components 230 to de-allocate virtual machine instances and/or content item instances from a content item fleet. These conditions may include for example, determining that the total and/or average number of unoccupied user sessions for all content item instances in the fleet have met or exceeded a particular quantity, determining that the total number of unoccupied user sessions for one or more individual content item instances in the fleet have met or exceeded a particular quantity, and/or other conditions. Also, in some examples, scaling components 230 may de-allocate virtual machine instances and/or content item instances from a content item fleet based on a determination that a particular sub-set of a content item fleet, such as a sub-set of content item instances having particular content attributes (e.g., modes, virtual locations, characters, weapons, plot lines, story arcs, etc.) satisfies any of the example de-allocation conditions described above or other conditions. The de-allocated virtual machine may then eventually be terminated and/or re-purposed. It is noted that, in some cases, it may not be advantageous to terminate and/or re-purpose a particular virtual machine instance immediately upon determining that a de-allocation condition has occurred. This is because the virtual machine instance selected for de-allocation may still be executing content item instances with assigned user sessions. In some examples, a determination may be made to stop assigning additional user sessions to content item instances on the virtual machine instance that is selected for de-allocation. The de-allocated virtual machine instance may then be terminated and/or re-purposed once the currently existing user sessions have expired.

Figure 3:
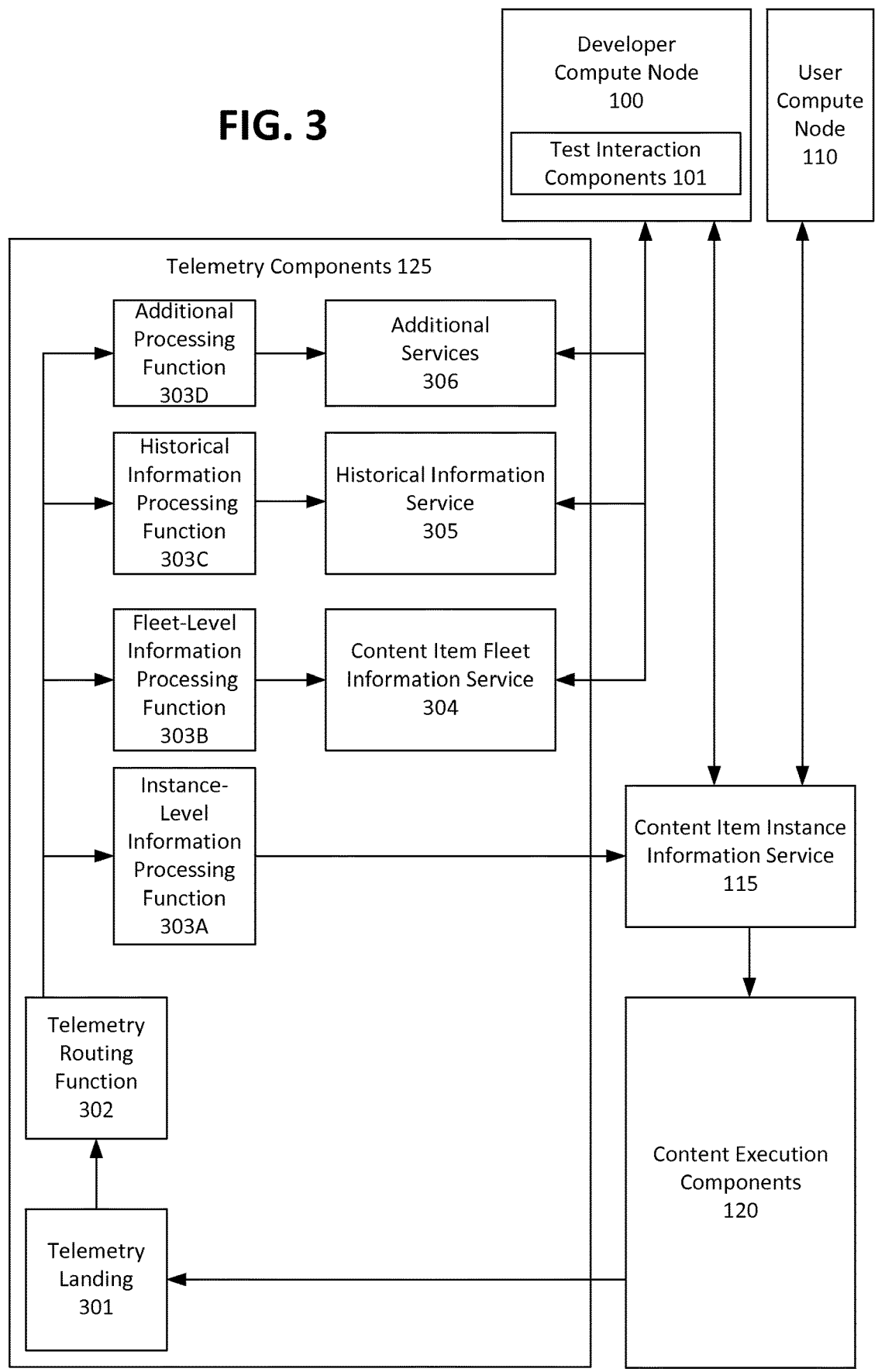
FIG. 3 is a diagram illustrating an example telemetry information routing and processing system that may be used in accordance with the present disclosure.

As set forth above, in addition to providing information to scaling components 230, proxy components 203 and 223 may provide information to telemetry landing 301. This information may be routed and processed by various telemetry components, which are now described in detail. In particular, FIG. 3 is a diagram illustrating an example telemetry information routing and processing system that may be used in accordance with the present disclosure. As shown in FIG. 3, information provided by content execution components 120 (including, for example, proxy components 203 and 223, as shown in FIG. 2) may be delivered to telemetry landing 301 of telemetry components 125 (also shown in FIG. 1). Upon being delivered to telemetry landing 301, telemetry information may be accessed by telemetry routing function 302, which may generally examine the provided information and, based on various factors, route the provided information to one or more recipients, such as processing functions 303A-D. In particular, instance-level processing function 303A receives and processes information for content item instance information service 115 (also shown in FIGS. 1 and 2). Fleet-level information processing function 303B receives and processes information for content item fleet information service 304. Historical information processing function 303C receives and processes information for historical information service 305. Additionally, telemetry routing function 302 may route information to any number of additional processing functions 303D that may receive and process information for any number of additional services 306.

In some examples, when writing telemetry information to telemetry landing 301, proxy components 203 and 223 may tag or otherwise identify the information with certain keys or other identification information according to a set of conventions. These conventions may assist the telemetry routing function 302 to quickly and efficiently route the telemetry information to appropriate recipients. For example, in some cases, the telemetry information may be identified using the following format: fleet identifier/instance identifier/route identifier/timestamp/globally unique identifier (GUID). The fleet identifier may be an identifier for the particular content item fleet with which the information is associated. The instance identifier may be an identifier for the particular content item instance with which the information is associated. The route identifier may be an identifier that indicates one or more recipients (e.g., any or all of processing functions 303A-D) to which the information should be sent. The timestamp may be a timestamp associated with the information, such as a time at which the information is collected. In some cases, this identification information may be all that is required for the telemetry routing function 302 to route respective telemetry information to the appropriate recipients.

In some examples, any of telemetry routing function 302 and/or processing functions 303A-D may be distributed computing-based (e.g., cloud-based) functions that execute code based, at least in part, on events, such as the receiving of telemetry information for routing and/or processing. For example, in some cases, telemetry routing function 302 may detect and/or may be informed of the receiving of telemetry information at telemetry landing 301. In response to this, telemetry routing function 302 may automatically initiate execution of code for routing the telemetry information, based on, for example, the identification information such as described above. Likewise, processing functions 303A-D may then detect and/or may be informed of telemetry information that has been routed thereto, and may then automatically initiate execution of code for processing the received information, such as by organizing and storing the received information and generating any appropriate alarms or notifications. In some examples, implementation of telemetry routing function 302 and/or processing functions 303A-D using distributed computing-based (e.g., cloud-based) functions that execute code based, at least in part, on events may be advantageous by, for example, reducing the amount of computing resources and cost that may be required for routing and/or processing services that maintained a constant execution even during times when no new telemetry information was available for routing and/or processing.

Content item instance information service 115 may generally receive and provide information regarding individual content item instances executed by content execution components 120, including, for example, content item instances 201A-N and 221A-N of FIG. 2. This information may include, for example, a number of occupied user sessions for each executing content item instance, a number of unoccupied user sessions for each executing content item instance, content item instance duration information, memory usage by in each executing content item instance, and the like. Content item instance information service 115 may use this information, for example, to assist in matching and assigning of user sessions to particular content item instances. In particular, referring back to FIG. 1, it is seen that content client 112 of user compute node 110 may communicate with content item instance information service 115 to request information about available content and to request access to available content. As also shown in FIG. 1, content item instance information service 115 may communicate with identity and entitlement services 105 to determine, based at least in part on entitlement information 106, which content items the user is entitled to access. It is noted that entitlement information 106 may indicate user entitlements at various different levels of granularity. For example, in some cases, entitlement information 106 may indicate whether the user is generally allowed access to the content executed by system 150. In other cases, entitlement information 106 may be provided at finer granularity levels and may indicate particular content to which the user is entitled to access, such as particular titles, particular versions, particular story arcs or plotlines, particular virtual locations, particular modes, particular characters, particular weapons, and the like.

In some examples, content client 112 may request that content item instance information service 115 provide information about available content items that the user is entitled to access, such as a listing of all available content items or content items having certain content attributes, such as certain plot lines, story arcs, virtual locations, levels, modes, characters, weapons, and the like. Upon receiving this information, in some examples, the user may select a particular content item and submit a request to access to selected content item via content client 112. Additionally, content client 112 may also provide to content item instance information service 115 information about certain content preferences desired by the user, such as certain plot lines, story arcs, virtual locations, levels, modes, characters, weapons, and the like. Content item instance information service 115 may then, based at least in part on the user's request, the user's preferences, and the telemetry information received from telemetry components 125, match the user's request to a particular instance of the user's selected content item.

In some examples, content item instance information service 115 may attempt to identify one or more instances of the selected content item having content attributes that match, or at least partially match, content attributes of the user's requested preferences. Content item instance information service 115 may obtain content attribute information for executing content item instances through a variety of different techniques. In some examples, content attribute information may be collected and provided as part of telemetry information made available from telemetry components 125, may be retrieved from scaling component 230 of FIG. 2, or may be otherwise made available to content item instance information service 115. Upon identifying one or more content item instances with content attributes that at least partially match the user's preferences, content item information service may then determine, based at least in part on telemetry information from telemetry components 125, whether there are any unoccupied user sessions for any of the identified content item instances. In some examples, content item instance information service 115 may then assign the user to one of the identified content item instances with at least one unoccupied user session. In some examples, the user may be assigned to the identified content item instance with at least one unoccupied user session that has content attributes that most closely matches the user's preferences. In other examples, the user may be assigned to a content item instance based on a combination of factors including, for example, the user's preferences, a number of unoccupied user sessions, and the like. For example, consider the scenario in which a user specifies five different content attribute preferences for a content item instance to join. Now suppose that a first content item instance matches all five of the user's preferences but only has one unoccupied user session, while a second content item instance matches four out of five of the user's preferences but has ten unoccupied user sessions. In this scenario, it may be advantageous to assign the user to the second content item instance, in order to keep the single remaining unoccupied user session of the first content item instance available for other users whose preferences may be even more strongly correlated to the first content item instance. Also, in some examples, content item instance information service 115 may provide information about identified content item instances with at least one unoccupied user session that at least partially match a user's preferences to content client 112 in order to allow the user to select one of the identified content item instances for assignment or to otherwise provide input for making such a selection.

In some examples, content item instance information service 115 may, instead of matching and assigning the user to an existing already launched and executing content item instance, request that scaling components 230 launch an additional content item instance to which to assign the user. This may occur, for example, when none of the existing content item instances within the fleet have any remaining unoccupied user sessions and/or when none of the existing content item instances within the fleet have content attributes that are determined to sufficiently match the user's requested content attribute preferences.

Once the user has been matched and assigned to a particular content item instance, content item instance information service 115 may provide an indication of the assigned content item instance (or instructions to launch a new content item instance) to scaling components 230. Scaling components 230 may, in turn, establish communications between a user session for the user and the assigned content item instance by, for example, instructing the assigned content item instance to communicate with content client 112 at user compute node 110. As set forth above, in some examples, these communications may include transmitting, by the assigned content item instance, state information, event information, rendered graphics and audio, and/or other information associated with the content item instance to the content client 112 corresponding to the user session. Also, in some examples, these communications may include transmitting, by the content client 112, input, such as control input (e.g., character movement, weapons firing, menu selections, etc.) to the assigned content item instance.

Thus, as described above, content item instance information service 115 may use content item instance-level telemetry information provided by telemetry components 125 to assist in the process of matching and assigning users sessions to content item instances. In addition to these matching techniques, content item instance-level telemetry information provided to content item instance information service 115 may also be used, for example, to provide content item instance-level feedback and metrics to developers and possibly other parties. In particular, as shown in both FIGS. 1 and 3, developer compute node 100 may access content item instance information service 115 to request content item instance-level information, such as a number of occupied user sessions for each executing content item instance, a number of unoccupied user sessions for each executing content item instance, content item instance duration information, memory usage by in each executing content item instance, and the like.

Referring back to FIG. 3, in addition to content item instance information service 115, telemetry routing function 302 may route telemetry information, though respective processing functions 303B-D, to content item fleet information service 304, historical information service 305, and other additional services 306. Content item fleet information service 304 may generally receive and provide content item fleet-level telemetry information to developers and/or other parties. Content item fleet-level information may include information regarding occupied user sessions within the fleet, unoccupied user sessions within the fleet, instance duration information for the fleet, memory usage by the fleet, a number of executing instances within the fleet, instance termination information, and the like. For occupied user sessions, the fleet-level information may include, for example, the total number of occupied user sessions for all fleet instances, an average number of occupied user sessions for all fleet instances, a number of occupied sessions in the fleet instance with the least occupied sessions, a number of occupied sessions in the fleet instance with the most occupied sessions and the like. For unoccupied user sessions, the fleet-level information may include, for example, the total number of unoccupied user sessions for all fleet instances, an average number of unoccupied user sessions for all fleet instances, a number of unoccupied sessions in the fleet instance with the least unoccupied sessions, a number of unoccupied sessions in the fleet instance with the most unoccupied sessions and the like. For instance duration information, the fleet-level information may include, for example, total, average, maximum, and minimum duration for fleet instances that terminated within a particular period as well as a number of instances that terminated within a particular period. For memory usage information, the fleet-level information may include, for example, total, average, maximum, and minimum memory usage for fleet instances.

In some examples, content item fleet information service 304 and/or content item instance information service 115 may allow developers or other parties to set alarms and/or other notifications such that they may be notified of certain events or conditions associated with content item fleets and/or instances. Some example conditions that may trigger alarms are a total number of occupied fleet sessions meeting, exceeding or falling below specified levels, one or more fleet instances having less than a specified number of occupied sessions, a total number of unoccupied fleet sessions meeting, exceeding or falling below specified levels, fleet instances having less than a specified average time duration, fleet instances having more than a specified average or maximum memory usage, and other conditions.

Historical information service 305 may generally receive, maintain, and provide historical information regarding content item fleets and/or content item instances. In some examples, historical information service may include historical information about content item fleets and/or content item instances that have been previously terminated and/or information about content item fleets and/or content item instances that may wholly are partially continue to be executed. Historical information service 305 may, for example, provide any, or all, of the instance-level information and or fleet-level information set forth in detail above and/or any other relevant historical information. In some examples, historical information may allow developers and/or other parties to request information for certain specifiable historical periods, such as for the past sixty or ninety days, or any other relevant period.

Figure 4:
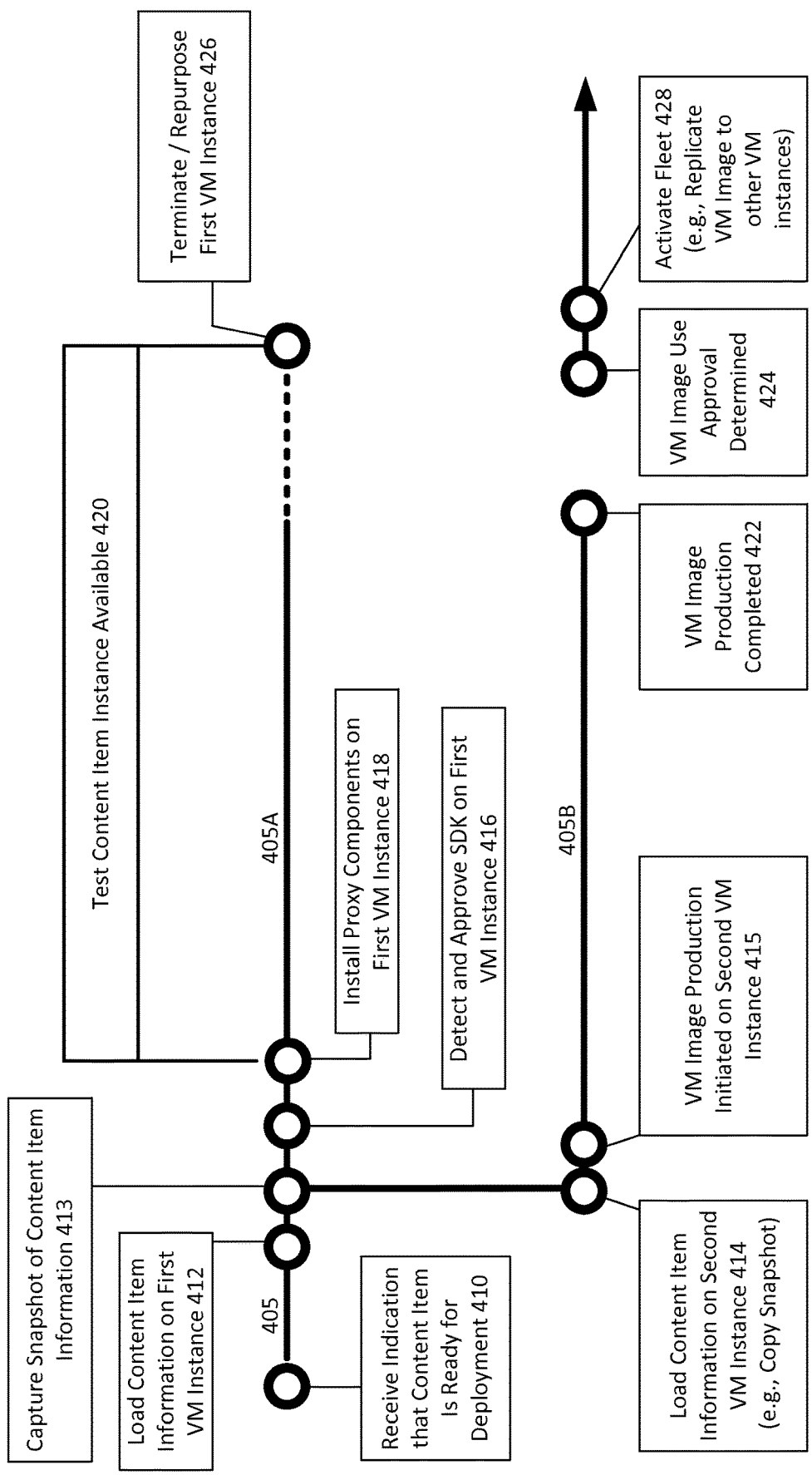
FIG. 4 is a diagram illustrating an example content item testing and deployment timeline that may be used in accordance with the present disclosure.

Some example techniques for testing and deployment of a content item will now be described in detail. In particular, FIG. 4 is a diagram illustrating an example content item testing and deployment timeline 405 that may be used in accordance with the present disclosure. It is noted that the timeline 405 is not drawn to scale and is not intended to depict any particular exact amounts of time occurring before, during, or after any particular events. As shown in FIG. 4, at event 410, an indication is received that a content item, such as a video game, is ready for deployment on, for example, a backend service. The indication may be received from a developer of the content item. The content item information may include information associated with the content item, such as code, binary files, developer install scripts, and other information associated with the content item. In addition to the indication received at event 410, a developer may also provide, for example, an indication of one or more locations at which content item information may be stored and retrieved from. A developer may also provide, for example, a name for a fleet of instances of the content item, a stage of development for the content item, a description of the content item, and other information.

Upon receiving the indication that the content item is ready for deployment, the backend service may locate the associated content item information based on, for example, location information provided by the developer. At event 412, the service may then load the content item information on to first a virtual machine instance. The process of loading the content item information may include, for example, loading of code and/or binary files associated with the content item and execution of developer install scripts associated with the content item.

Upon completion of the loading of the content item information, a snapshot (i.e., a copy) of the loaded content item information, or any portions thereof, may be captured. Upon performance of event 413, the timeline 405 forks into an upper portion 405A and a lower portion 405B. The forking of timeline 405 in this manner is intended to convey that portions 405A and 405B may be performed in parallel or partially in parallel with one another. At event 414, content item information is loaded on a second virtual machine instance, such as by copying the snapshot created at event 413 to the second virtual machine instance. At event 415, the virtual machine image production process is initiated on the second virtual machine instance. The virtual machine image production process may include generating of the virtual machine image based, at least in part, on the content item information that is loaded onto the second virtual machine instance. Accordingly, the virtual machine image may include the content item information loaded onto the second virtual machine instance. Additionally, as will be described below, each replica of the virtual machine image may also include the content item information loaded onto the second virtual machine instance. In some examples, the virtual machine image may include a read-only file system image with an operating system. Also, in some examples, the virtual machine image may be signed, encrypted, compressed, and divided into various portions or chunks of information. In some examples, the virtual machine image may be an Amazon machine image (AMI). The duration of time required to produce the virtual machine image may sometimes be based, at least in part, on the amount of information that is being included within the virtual machine image. For example, a virtual machine image that includes a larger quantity of information may typically require more time to produce than a virtual machine image that includes a smaller quantity of information.

Referring back to upper timeline portion 405A, it is seen that, after taking the snapshot of the content item information, an SDK may be detected and approved on the first virtual machine instance at event 416. In some examples, it may be necessary to shut down and re-start the test virtual machine instance between performance of events 413 and 416. As set forth above, in some examples, one or more services that host deployed instances of the content item may expose one or more SDK's that are integrated with the one or more services. In these examples, the SDK's may provide code and other functionality built-in to the content item that may allow, for example, ingestion, configuration, provisioning and deployment of the content to be more easily and rapidly accomplished, such as by allowing the content to interact more efficiently with a multi-player video gaming or other multi-user environment. For example, an SDK used to create the content may assist in configuration of new user sessions for one or more users and reporting and collection of information about executing content item instances, such as a number of occupied user sessions, a number of unoccupied user sessions, content item instance duration, memory usage, and the like.

Accordingly, at event 416, the content item information on the first virtual machine instance may be examined to confirm that the content item has been created using an approved SDK and to detect of a particular version of the SDK that was used to create the content item. An approved SDK in this context may be an SDK that is integrated with a backend service that will potentially host the activated content item fleet. An SDK may be approved at event 416 by, for example, examining the content item information on the first virtual machine instance to identify various instructions that match or are otherwise associated with an approved SDK. In some examples, an approved SDK may be capable of reporting information to or otherwise interacting with an instance interface of a content deployment service, such as instance interfaces 202A-N and 222A-N of FIG. 2. Also, in some examples, a particular version of an instance interface to use with deployed instances of the content item may be determined based on the version of the SDK detected within the content item information at event 416. It is noted that, by detecting and approving an SDK on the first virtual machine instance, it may not be necessary to subsequently detect and approve an SDK on the virtual machine image or on replicas thereof.

In some examples, if an approved SDK cannot be detected within the content item information on the first virtual machine instance, then it may be determined that the content item is not currently suitable for hosting by the service. The developer may be informed of this error and asked to edit or recreate the content item such that it includes an approved SDK. In such cases, use of the first virtual machine instance and the virtual machine image may be disapproved and/or terminated.

At event 418, proxy components are installed on the first virtual machine instance. The proxy components installed at event 418 may, for example, be similar or identical to proxy components 203 and 223 of FIG. 2. As set forth above, such proxy components may generally allow exchange of information and commands between executing content item instances and other components, such as scaling components 230 and telemetry landing 301 of FIG. 2. The function and operation of proxy components 203 and 223 is described in detail above and is not repeated here.

As shown in FIG. 4, after SDK detection and approval (event 416) and proxy component installation (event 418), a content item instance executed on the first virtual machine instance, referred to herein the test content item instance, may become available for execution during time period 420. In particular, during any portions of time period 420, one or more user sessions may be assigned and connected to the test content item instance. In some examples, the one or more connected user sessions may be operated by a developer of the content item for the purposes of testing or otherwise interacting with the content item. As shown in FIG. 4, the test content item instance is made available for execution during at least part of the virtual machine image production time (i.e., the time between events 414 and 422 on timeline portion 405B). As set forth above, execution and testing of the content item using the test content item instance may, in some cases, allow developers to test and interact with a content item instance that is executed by the same backend service that will potentially host the activated content item fleet, thereby allowing developers to test and interact with the content item in the same environment in which it may be provided to other users. In some cases, the test content item instance may allow testing of the content item such that one or more flaws or other problems may be quickly identified and efficiently corrected. Additionally, the test content item instance may, for example, allow developers to experience the benefits of the virtual machine image without having to wait until the image is fully produced in order to test or otherwise interact with the content item.

Referring back to lower timeline portion 405B, it is seen that the virtual machine image production may be completed at event 422. In some examples, upon completion of production of the virtual machine image, the developer may be informed that the virtual machine image production is complete and the virtual machine image is ready for use. Subsequently, at event 424, an approval to use the virtual machine image may be determined. For example, an approval to use the virtual machine image may be received from the developer. It is noted that there is no requirement that use of the virtual machine image must be approved by the developer immediately upon completion of the production of the virtual machine image. In the particular example of FIG. 4, there is a time delay between completion of the virtual machine image production (event 422) and determination of its approval for use (event 424). This time delay is indicated by the break in lower timeline portion 405B between events 422 and 424 and also by the dashed lines within upper timeline portion 405A between events 422 and 424. In some examples, during the time delay between events 422 and 424, the developer may continue to test and interact with the test content item instance even after production of the virtual machine image has completed.

In some examples, the approval and use of the virtual machine image may result in various costs to the developer, such as costs for acquiring and using virtual machine instances to which the virtual machine image is replicated. In some cases, the developer may not be certain that these costs are justified and that approval is desirable immediately at the point when the virtual machine image production is completed. Thus, in these and other cases, the developer may sometimes wish to continue to test and interact with the content item on the test content item instance even after the virtual machine image production is completed. This may allow the developer to conduct further testing and additional interaction with the content item prior to making a final decision on whether or not to approve the virtual machine image for use and incur the costs that may be associated with such approval.

In the example of FIG. 4, determining approval for use of the virtual machine image (event 424) triggers the performance of events 426 and 428. In particular, immediately or shortly after determining approval for use of the virtual machine image, the first virtual machine instance may be terminated or repurposed at event 426. As should be appreciated, once the first virtual machine instance has been terminated or repurposed, the test content item instance will cease to be available for execution, as indicated by the expiration of time period 420 at event 426.

Additionally, after determining approval for use of the virtual machine image, the content item fleet becomes activated at event 428. In particular, upon being activated, the content item fleet may be generated by replicating the virtual machine image to one or more other virtual machine instances. As set forth above, the virtual machine image may be advantageous because, for example, it may allow the content item to be easily and efficiently replicated onto large numbers of other virtual machines, thereby allowing large numbers of content item instances to scale up quickly in response to user demand.

It is noted that, in some examples, an explicit approval for use of the virtual machine image may not be required to be received from the developer. For example, a determination of the approval for use of the virtual machine image may sometimes be inferred without receiving an explicit approval from the developer. In some examples, approval for use of the virtual machine image may be inferred automatically upon completion of production of the virtual machine image, and the fleet may be activated.

Figure 5:
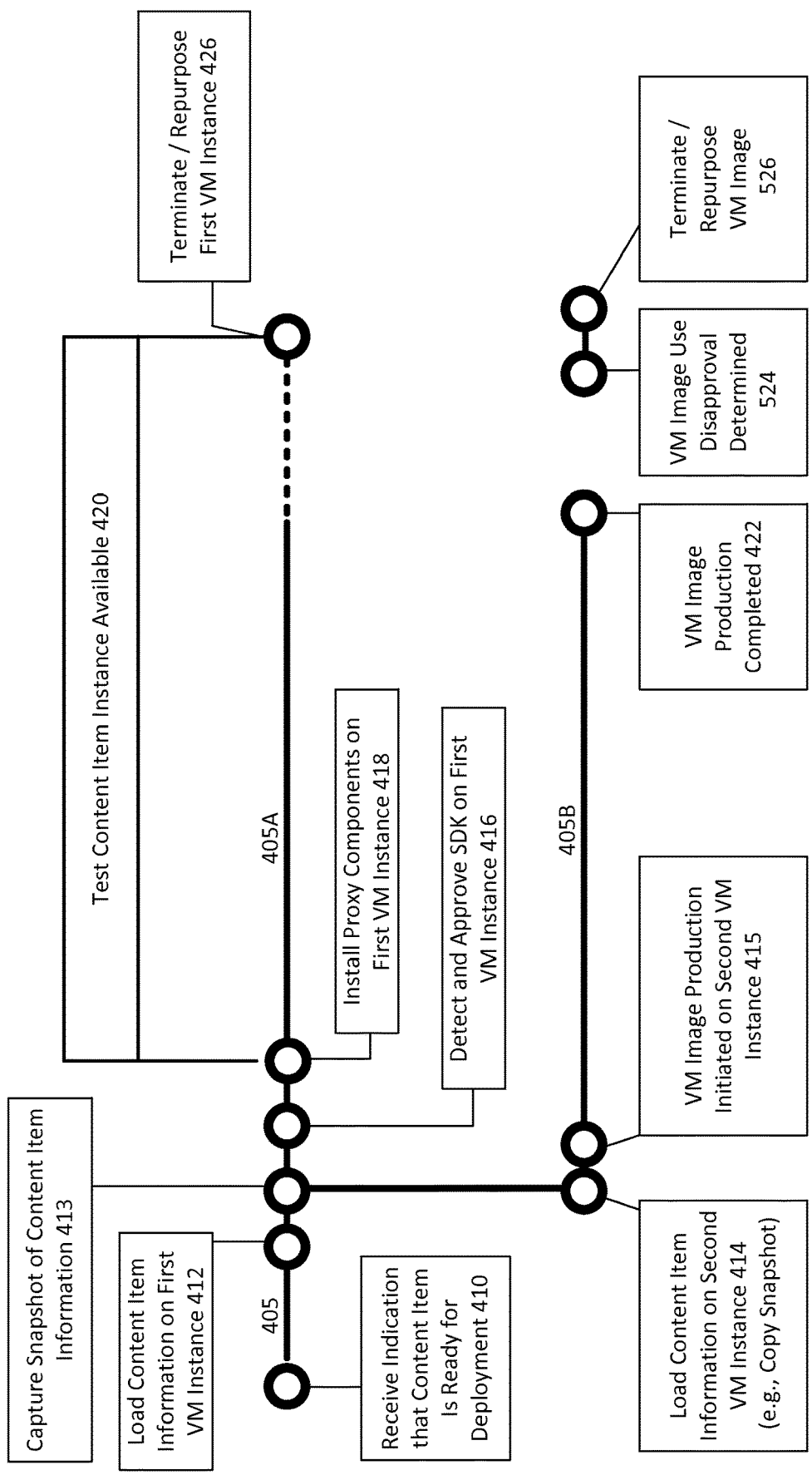
FIG. 5 is a diagram illustrating another example content item deployment process timeline that may be used in accordance with the present disclosure.

As set forth above, in some examples, a developer may choose not to approve use of the virtual machine image. This may occur, for example, when the developer determines, such as based on testing of the test content item instance, that they are not satisfied with the content item, do not wish incur the cost of fleet activation and execution, or otherwise do not wish to approve use of the virtual machine image. In some cases, the developer may send a message explicitly indicating that the content item fleet is not approved for activation. In other cases, disapproval of the fleet activation may sometimes be inferred based on factors such as expiration of a time period after completion of image production without receiving an explicit approval or other factors. FIG. 5 depicts an example in which the virtual machine image is not approved for use. In particular, FIG. 5 is identical to FIG. 4 up until the completion of the virtual machine image production at event 422. However, as shown in FIG. 5, subsequent to completion of the virtual machine image production, virtual machine image use disapproval is determined at event 524. As set forth above, event 524 may include receiving of an explicit disapproval or an inference of disapproval based on, for example, an expiration of a time period. Upon occurrence of event 524, the first virtual machine instance is terminated or repurposed (event 426) and the virtual machine image is also terminated or repurposed (event 526).

Figure 6:
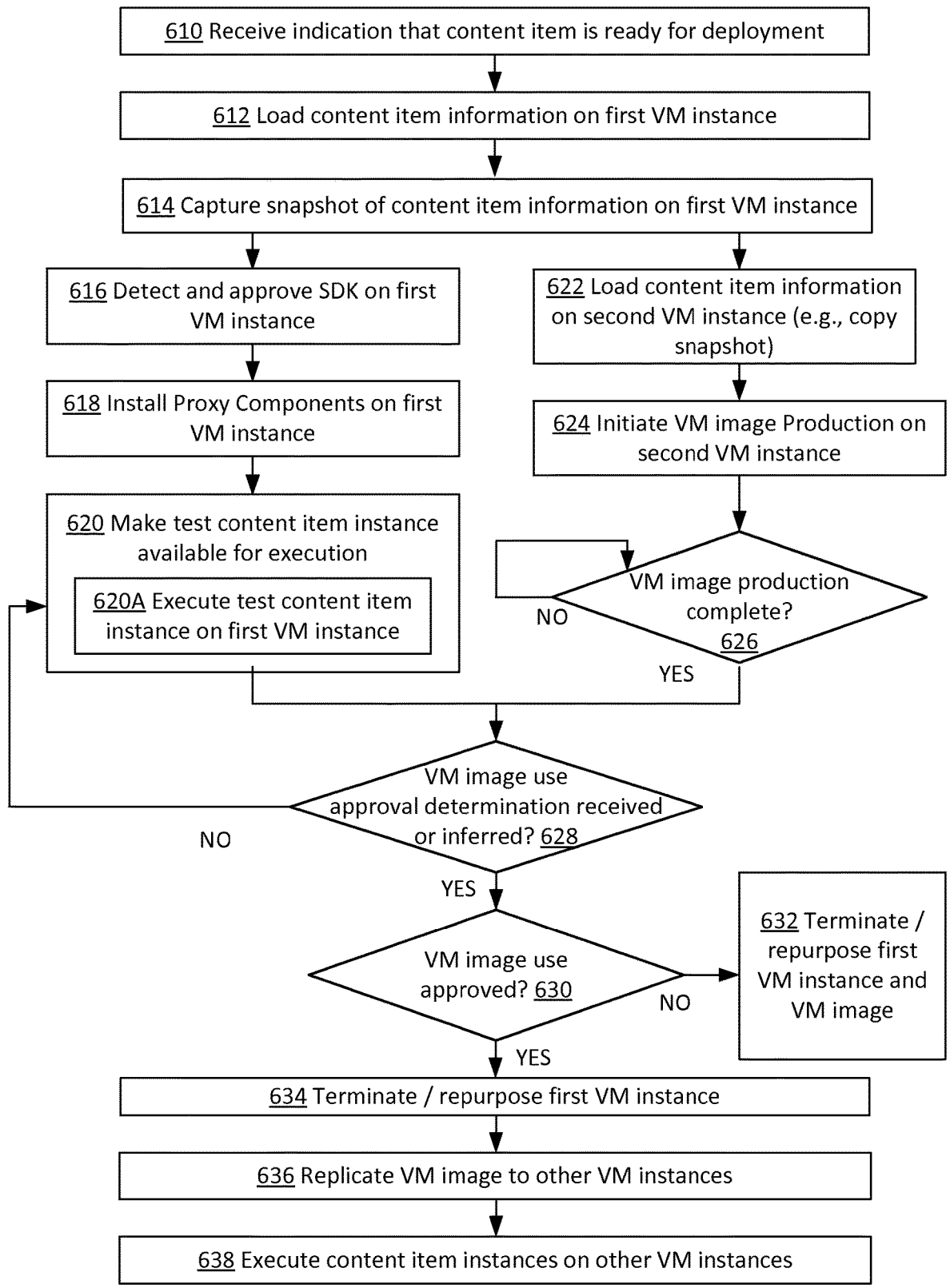
FIG. 6 is a diagram illustrating an example process for content item execution during production of a virtual machine image that may be used in accordance with the present disclosure.

FIG. 6 is a diagram illustrating an example process for content item execution during production of a virtual machine image that may be used in accordance with the present disclosure. As shown in FIG. 6, at operation 610, an indication is received (e.g., from a developer) that a content item, such as a video game, is ready for deployment. The content item information may include information associated with the content item, such as code, binary files, developer install scripts, and other information associated with the content item. As set forth above, a developer may also indicate one or more locations at which content item information may be stored and retrieved from.

Upon receiving the indication that the content item is ready for deployment, content item information associated with the content item may be loaded on to first a virtual machine instance at operation 612. As set forth above, the process of loading the content item information may include, for example, loading of code and/or binary files associated with the content item and execution of developer install scripts associated with the content item.

Upon completion of the loading of the content item information, a snapshot (i.e., a copy) of the loaded content item information, or any portions thereof, may be made at operation 614. At operation 622, content item information is loaded onto a second virtual machine instance, such as by copying the snapshot created at operation 614 to the second virtual machine instance or otherwise loading the content item information onto the second virtual machine instance. At operation 624, the virtual machine image production process is initiated on the second virtual machine instance. As set forth above, the virtual machine image production process may include generating of the virtual machine image based, at least in part, on the content item information that is loaded onto the second virtual machine instance. Accordingly, the virtual machine image, and each replica thereof, may include the content item information loaded onto the second virtual machine instance.

At operation 626, it is determined whether the virtual machine image production has completed. In some examples, an indication of the completion of production of the virtual machine image may be sent to the developer. Upon completion of the virtual machine image production, the process proceeds to operation 628, at which it is determined whether an approval to use the virtual machine image has been received (or inferred).

As shown in FIG. 6, it is seen that, after performance of operation 614, another series of operations (i.e., operations 616, 618 and 620) is performed in association with the first virtual machine image. In particular, at operation 616, an SDK may be detected and approved on the first virtual machine instance. As set forth above, the content item information on the first virtual machine instance may be examined to confirm that the content item has been created using an approved SDK and to detect of a particular version of the SDK that was used to create the content item. An approved SDK in this context may be an SDK that is integrated with a backend service that will potentially host the activated content item fleet. An SDK may be approved at operation 616 by, for example, examining the content item information on the first virtual machine instance to identify various instructions that match or are otherwise associated with an approved SDK.

At operation 618, proxy components are installed on the first virtual machine instance. As set forth above, such proxy components may generally allow exchange of information and commands between executing content item instances and other components, such as scaling components 230 and telemetry landing 301 of FIG. 2.

At operation 620, the test content item instance is made available for execution, such as by notifying a developer that the test content item instance is available for execution. At sub-operation 620A, the test content item instance is executed on the first virtual machine instance. At least part of the time during which the test content item instance is executed may occur during the production of the virtual machine image. As set forth above, the test content item instance may, for example, allow developers to experience the benefits of the virtual machine image without having to wait until the image is fully produced in order to test or otherwise interact with the content item. In some cases, the test content item instance may allow testing of the content item such that one or more flaws or other problems may be quickly identified and efficiently corrected. Additionally, execution and testing of the content item using the test content item instance may, in some cases, allow developers to test and interact with a content item instance that is executed by the same backend service that will potentially host the activated content item fleet, thereby allowing developers to test and interact with the content item in the same environment in which it may be provided to other users.

As shown in FIG. 6, the test content item instance may continue to be made available for execution (and may sometimes continue to be executed) at least until it is determined, at operation 628, that a virtual machine image use approval determination has been received or inferred (e.g., until the use of the virtual machine instance is approved or disapproved). As set forth above, there is no requirement that use of the virtual machine image must be approved by the developer immediately upon completion of the production of the virtual machine image. Rather, the developer may sometimes delay an approval determination and may continue to test and interact with the test content item instance even after production of the virtual machine image has completed. Accordingly, the process of FIG. 6 may continue to cycle through operations 628 and 620 until a virtual machine image use approval determination has been received or inferred. As set forth above, in some examples, operation 628 may include receiving a message from a developer that explicitly approves or disapproves of use of the virtual machine image. In other examples, approval or disapproval of use of the virtual machine image may be inferred. For example, in some cases, approval may be automatically inferred. In other cases, disapproval may be inferred if the developer fails to provide an explicit approval within a specified time period after completion of the virtual machine image production.

At operation 630, it is determined whether use of the virtual machine image is approved. If, at operation 630, it is determined that use of the virtual machine is not approved, then both the first virtual machine instance and the virtual machine image may be terminated and/or repurposed at operation 632.

If, on the other hand, at operation 630, it is determined that use of the virtual machine is approved, then operations 634, 636 and/or 638 may then be performed based, at least in part, on the approval of the virtual machine image for use. In particular, the process may proceed to operation 634, at which the first virtual machine instance may be terminated or repurposed. At operation 636, the virtual machine may be replicated to one or more other virtual machine instances. As set forth above, the virtual machine image may be advantageous because, for example, it may allow the content item to be easily and efficiently replicated onto large numbers of other virtual machines, thereby allowing large numbers of content item instances to scale up quickly in response to user demand. At operation 638, content item instances are executed on the other virtual machine instances to which the virtual machine image is replicated. These content item instances may form a scalable fleet of executing instances of the content item, thereby potentially allowing large numbers of users to simultaneously or partially simultaneously connect and interact with the content item. Accordingly, in some examples, the virtual machine image may be used on a plurality of virtual machine instances to host multiple users accessing the content item. For example, in some cases, the virtual machine image may be used on a plurality of virtual machine instances to allow hosting of multiple game sessions or other content item sessions in a cloud or other distributed computing environment.

Figure 7:
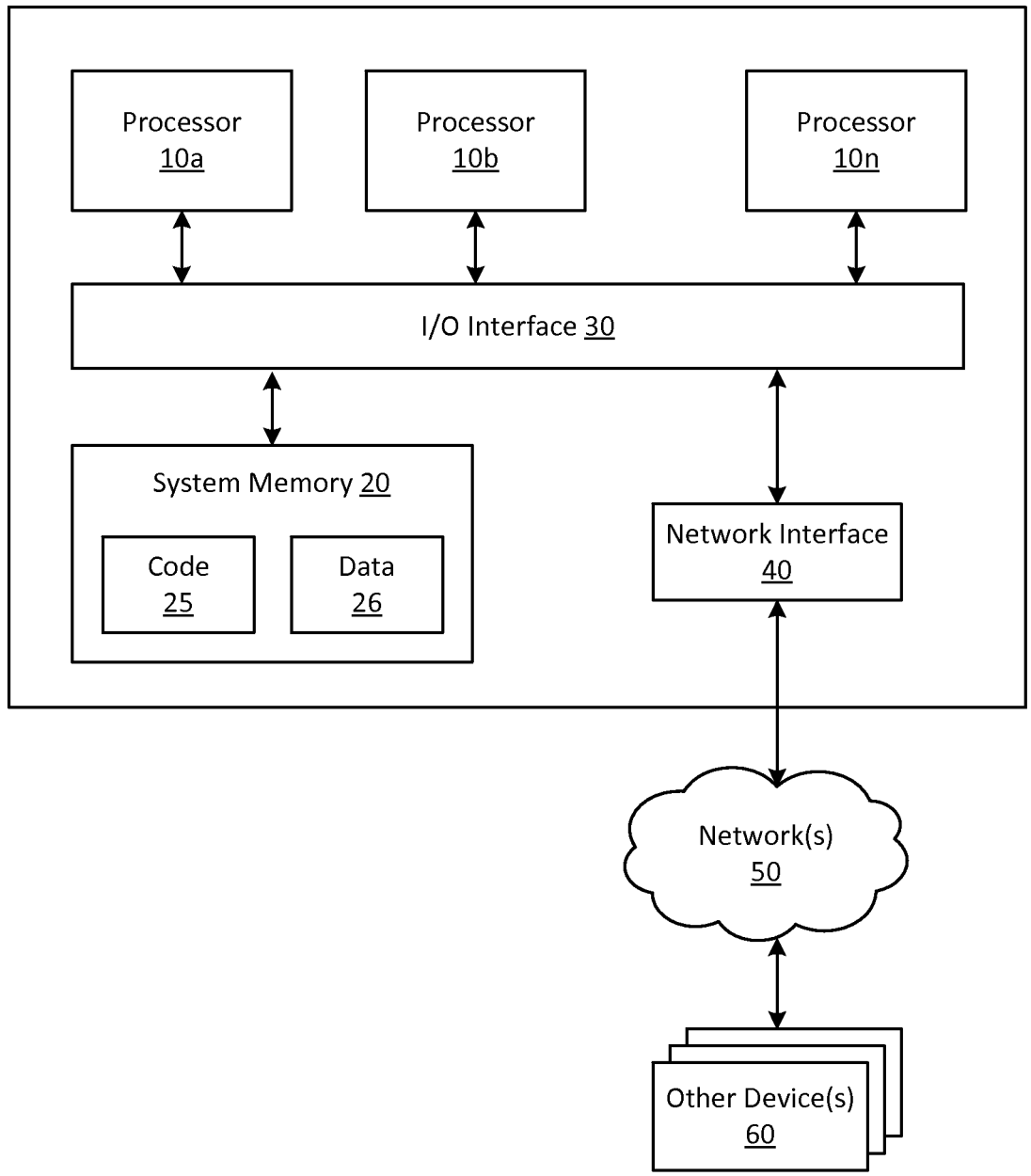
FIG. 7 is a diagram illustrating an example computing system that may be used in accordance with the present disclosure.

In at least some embodiments, one or more compute nodes that implement a portion or all of one or more of the technologies described herein may include or may be associated with a computer system that includes or is configured to access one or more computer the-accessible media. A compute node, which may be referred to also as a computing node, may be implemented on a wide variety of computing environments, such as commodity-hardware computers, virtual machines, web services, computing clusters and computing appliances. Any of these computing devices or environments may, for convenience, be described as compute nodes. FIG. 7 depicts a computer system that includes or is configured to access one or more computer-accessible media. In the illustrated embodiment, computing device 15 includes one or more processors 10*a*, 10*b* and/or 10*n* (which may be referred herein singularly as "a processor 10" or in the plural as "the processors 10") coupled to a system memory 20 via an input/output (I/O) interface 30. Computing device 15 further includes a network interface 40 coupled to I/O interface 30.

In various embodiments, computing device 15 may be a uniprocessor system including one processor 10 or a multiprocessor system including several processors 10 (e.g., two, four, eight or another suitable number). Processors 10 may be any suitable processors capable of executing instructions. For example, in various embodiments, processors 10 may be embedded processors implementing any of a variety of instruction set architectures (ISAs), such as the x86, PowerPC, SPARC or MIPS ISAs or any other suitable ISA. In multiprocessor systems, each of processors 10 may commonly, but not necessarily, implement the same ISA.

System memory 20 may be configured to store instructions and data accessible by processor(s) 10. In various embodiments, system memory 20 may be implemented using any suitable memory technology, such as static random access memory (SRAM), synchronous dynamic RAM (SDRAM), nonvolatile/Flash®-type memory or any other type of memory. In the illustrated embodiment, program instructions and data implementing one or more desired functions, such as those methods, techniques and data described above, are shown stored within system memory 20 as code 25 and data 26.

In one embodiment, I/O interface 30 may be configured to coordinate I/O traffic between processor 10, system memory 20 and any peripherals in the device, including network interface 40 or other peripheral interfaces. In some embodiments, I/O interface 30 may perform any necessary protocol, timing or other data transformations to convert data signals from one component (e.g., system memory 20) into a format suitable for use by another component (e.g., processor 10). In some embodiments, I/O interface 30 may include support for devices attached through various types of peripheral buses, such as a variant of the Peripheral Component Interconnect (PCI) bus standard or the Universal Serial Bus (USB) standard, for example. In some embodiments, the function of I/O interface 30 may be split into two or more separate components, such as a north bridge and a south bridge, for example. Also, in some embodiments some or all of the functionality of I/O interface 30, such as an interface to system memory 20, may be incorporated directly into processor 10.

Network interface 40 may be configured to allow data to be exchanged between computing device 15 and other device or devices 60 attached to a network or networks 50, such as other computer systems or devices, for example. In various embodiments, network interface 40 may support communication via any suitable wired or wireless general data networks, such as types of Ethernet networks, for example. Additionally, network interface 40 may support communication via telecommunications/telephony networks, such as analog voice networks or digital fiber communications networks, via storage area networks such as Fibre Channel SANs (storage area networks) or via any other suitable type of network and/or protocol.

In some embodiments, system memory 20 may be one embodiment of a computer-accessible medium configured to store program instructions and data as described above for implementing embodiments of the corresponding methods and apparatus. However, in other embodiments, program instructions and/or data may be received, sent or stored upon different types of computer-accessible media. Generally speaking, a computer-accessible medium may include non-transitory storage media or memory media, such as magnetic or optical media—e.g., disk or DVD/CD coupled to computing device 15 via I/O interface 30. A non-transitory computer-accessible storage medium may also include any volatile or non-volatile media, such as RAM (e.g., SDRAM, DDR SDRAM, RDRAM, SRAM, etc.), ROM (read only memory) etc., that may be included in some embodiments of computing device 15 as system memory 20 or another type of memory. Further, a computer-accessible medium may include transmission media or signals such as electrical, electromagnetic or digital signals conveyed via a communication medium, such as a network and/or a wireless link, such as those that may be implemented via network interface 40. Portions or all of multiple computing devices, such as those illustrated in FIG. 7, may be used to implement the described functionality in various embodiments; for example, software components running on a variety of different devices and servers may collaborate to provide the functionality. In some embodiments, portions of the described functionality may be implemented using storage devices, network devices or special-purpose computer systems. The term "computing device," as used herein, refers to at least all these types of devices and is not limited to these types of devices.

Each of the processes, methods and algorithms described in the preceding sections may be embodied in, and fully or partially automated by, code modules executed by one or more computers or computer processors. The code modules may be stored on any type of non-transitory computer-readable medium or computer storage device, such as hard drives, solid state memory, optical disc and/or the like. The processes and algorithms may be implemented partially or wholly in application-specific circuitry. The results of the disclosed processes and process steps may be stored, persistently or otherwise, in any type of non-transitory computer storage such as, e.g., volatile or non-volatile storage.

The various features and processes described above may be used independently of one another, or may be combined in various ways. All possible combinations and subcombinations are intended to fall within the scope of this disclosure. In addition, certain methods or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel or in some other manner. Blocks or states may be added to or removed from the disclosed example embodiments. The example systems and components described herein may be configured differently than described. For example, elements may be added to, removed from or rearranged compared to the disclosed example embodiments.

It will also be appreciated that various items are illustrated as being stored in memory or on storage while being used, and that these items or portions thereof may be transferred between memory and other storage devices for purposes of memory management and data integrity. Alternatively, in other embodiments some or all of the software modules and/or systems may execute in memory on another device and communicate with the illustrated computing systems via inter-computer communication. Furthermore, in some embodiments, some or all of the systems and/or modules may be implemented or provided in other ways, such as at least partially in firmware and/or hardware, including, but not limited to, one or more application-specific integrated circuits (ASICs), standard integrated circuits, controllers (e.g., by executing appropriate instructions, and including microcontrollers and/or embedded controllers), field-programmable gate arrays (FPGAs), complex programmable logic devices (CPLDs), etc. Some or all of the modules, systems and data structures may also be stored (e.g., as software instructions or structured data) on a computer-readable medium, such as a hard disk, a memory, a network or a portable media article to be read by an appropriate drive or via an appropriate connection. The systems, modules and data structures may also be transmitted as generated data signals (e.g., as part of a carrier wave or other analog or digital propagated signal) on a variety of computer-readable transmission media, including wireless-based and wired/cable-based media, and may take a variety of forms (e.g., as part of a single or multiplexed analog signal, or as multiple discrete digital packets or frames). Such computer program products may also take other forms in other embodiments. Accordingly, the present invention may be practiced with other computer system configurations.

Conditional language used herein, such as, among others, "can," "could," "might," "may," "e.g." and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having" and the like are synonymous and are used inclusively, in an open-ended fashion, and do not exclude additional elements, features, acts, operations and so forth.

Also, the term "or" is used in its inclusive sense (and not in its exclusive sense) so that when used, for example, to connect a list of elements, the term "or" means one, some or all of the elements in the list.

While certain example embodiments have been described, these embodiments have been presented by way of example only and are not intended to limit the scope of the inventions disclosed herein. Thus, nothing in the foregoing description is intended to imply that any particular feature, characteristic, step, module or block is necessary or indispensable. Indeed, the novel methods and systems described herein may be embodied in a variety of other forms; furthermore, various omissions, substitutions and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

What is claimed is:

1. A system for testing of a content item during production of a virtual machine image comprising:
   one or more computing devices; and
   one or more memories having stored thereon computer-executable instructions that, upon execution, cause the system to perform operations comprising:
      loading first information associated with the content item onto a first virtual machine instance;
      loading second information associated with the content item onto a second virtual machine instance, wherein the first information and the second information are identical;
      initiating, on the second virtual machine instance, the production of the virtual machine image, wherein the virtual machine image includes the second information associated with the content item and is signed and compressed;
      examining the first virtual machine instance to confirm that the content item has been created using a software development kit of a backend service that hosts execution of the content item;
      executing, on the first virtual machine instance, a first instance of the content item, wherein at least part of a time during which the first instance of the content item is executed occurs during the production of the virtual machine image, and wherein the first instance of the content item allows testing of the content item while the virtual machine image that is signed and compressed is being produced on the second virtual machine instance;
      completing the production of the virtual machine image;
      replicating the virtual machine image to one or more other virtual machine instances; and
      executing one or more other instances of the content item on the one or more other virtual machine instances, wherein the one or more other instances of the content item include instructions provided by the software development kit.

2. The system of claim 1, wherein the operations further comprise determining an approval for use of the virtual machine image, wherein the replicating of the virtual machine image is performed based, at least in part, on the approval.

3. The system of claim 1, wherein the operations further comprise, prior to executing the first instance of the content item, installing one or more proxy components on the first virtual machine instance.

4. A computer-implemented method for testing of a content item during production of a virtual machine image comprising:
   loading first information associated with the content item onto a first virtual machine instance;
   loading second information associated with the content item onto a second virtual machine instance, wherein the first information and the second information are identical;
   initiating, on the second virtual machine instance, the production of the virtual machine image, wherein the virtual machine image includes the second information associated with the content item and is signed and compressed;
   examining the first virtual machine instance to confirm that the content item has been created using a software development kit of a backend service that hosts execution of the content item;
   executing, on the first virtual machine instance, a first instance of the content item, wherein at least part of a time during which the first instance of the content item is executed occurs during the production of the virtual machine image, and wherein the first instance of the content item allows testing of the content item while the virtual machine image that is signed and compressed is being produced on the second virtual machine instance;
   completing the production of the virtual machine image;
   replicating the virtual machine image to one or more other virtual machine instances; and
   executing one or more other instances of the content item on the one or more other virtual machine instances, wherein the one or more other instances of the content item include instructions provided by the software development kit.

5. The computer-implemented method of claim 4, further comprising determining an approval for use of the virtual machine image, wherein the replicating of the virtual machine image is performed based, at least in part, on the approval.

6. The computer-implemented method of claim 5, further comprising terminating or repurposing the first virtual machine instance based, at least in part, on the approval.

7. The computer-implemented method of claim 5, wherein the first instance of the content item is available for execution at least until receiving or inferring the approval.

8. The computer-implemented method of claim 5, wherein the virtual machine image is used on a plurality of virtual machine instances to host multiple users accessing the content item.

9. One or more non-transitory computer-readable storage media having stored thereon instructions that, upon execution on at least one compute node, cause the at least one compute node to perform operations comprising:
   loading first information associated with a content item onto a first virtual machine instance;
   loading second information associated with the content item onto a second virtual machine instance, wherein the first information and the second information are identical;
   initiating, on the second virtual machine instance, the production of the virtual machine image, wherein the virtual machine image includes the second information associated with the content item and is encrypted and compressed;

examining the first virtual machine instance to confirm that the content item has been created using a software development kit of a backend service that hosts execution of the content item;

executing, on the first virtual machine instance, a first instance of the content item, wherein at least part of a time during which the first instance of the content item is executed occurs during the production of the virtual machine image, and wherein the first instance of the content item allows testing of the content item while the virtual machine image that is encrypted and compressed is being produced on the second virtual machine instance;

completing the production of the virtual machine image;

replicating the virtual machine image to one or more other virtual machine instances; and executing one or more other instances of the content item on the one or more other virtual machine instances, wherein the one or more other instances of the content item include instructions provided by the software development kit.

10. The one or more non-transitory computer-readable storage media of claim 9, wherein the operations further comprise, prior to executing the first instance of the content item, installing one or more proxy components on the first virtual machine instance.

11. The one or more non-transitory computer-readable storage media of claim 9, wherein the operations further comprise determining an approval for use of the virtual machine image, wherein the replicating of the virtual machine image is performed based, at least in part, on the approval.

12. The one or more non-transitory computer-readable storage media of claim 11, wherein the operations further comprise terminating or repurposing the first virtual machine instance based, at least in part, on the approval.

13. The one or more non-transitory computer-readable storage media of claim 11, wherein the first instance of the content item is available for execution at least until receiving or inferring the approval.

14. The one or more non-transitory computer-readable storage media of claim 9, wherein the virtual machine image is used on a plurality of virtual machine instances to host multiple users accessing the content item.

* * * * *